United States Patent
Hammett et al.

[11] Patent Number: 5,352,202
[45] Date of Patent: Oct. 4, 1994

[54] NON-REUSABLE SYRINGE WITH REMOVABLE PLUNGER USABLE AS A NEEDLE GUARD

[76] Inventors: Roy Hammett, 16103 Carden Dr., Odessa, Fla. 33556; Eric J. Sundsvold, 5121 Ironton Way, Englewood, Colo. 80111

[21] Appl. No.: 42,386

[22] Filed: Apr. 2, 1993

Related U.S. Application Data

[63] Continuation-in-part of Ser. No. 985,301, Dec. 4, 1992, abandoned, which is a continuation-in-part of Ser. No. 802,628, Dec. 5, 1991, Pat. No. 5,181,912.

[51] Int. Cl.⁵ ............................................... A61M 5/00
[52] U.S. Cl. .................................... 604/110; 604/192
[58] Field of Search ............... 604/110, 187, 192, 263, 604/218, 228, 194

[56] References Cited

U.S. PATENT DOCUMENTS

| | | | |
|---|---|---|---|
| 2,578,394 | 12/1951 | Blackman | 604/194 |
| 2,725,057 | 11/1955 | Lockhart | 604/193 |
| 5,084,027 | 1/1992 | Bernard | 604/263 X |
| 5,149,323 | 9/1992 | Colonna | 604/110 |
| 5,171,303 | 12/1992 | DeCamp | 604/192 |

*Primary Examiner*—John D. Yasko
*Attorney, Agent, or Firm*—Dennis H. Lambert

[57] ABSTRACT

A disposable hypodermic syringe having a barrel with an adapter on one end for attachment of a needle, and a piston and plunger reciprocable in the barrel. The plunger has a longitudinally extending hollow bore therein and is removable from the barrel and lockable on the adapter in enclosing relationship to the needle to serve as a needle guard. In one form of the invention, the piston and plunger are automatically separable upon use to prevent reuse of the syringe.

10 Claims, 7 Drawing Sheets

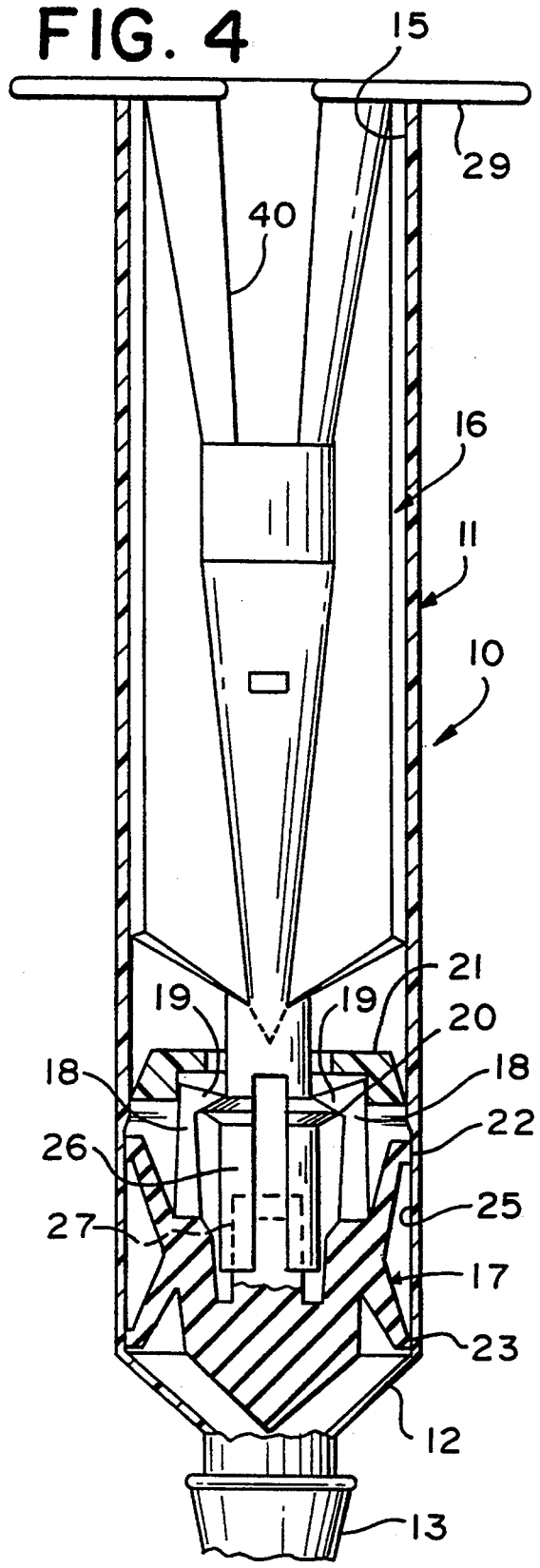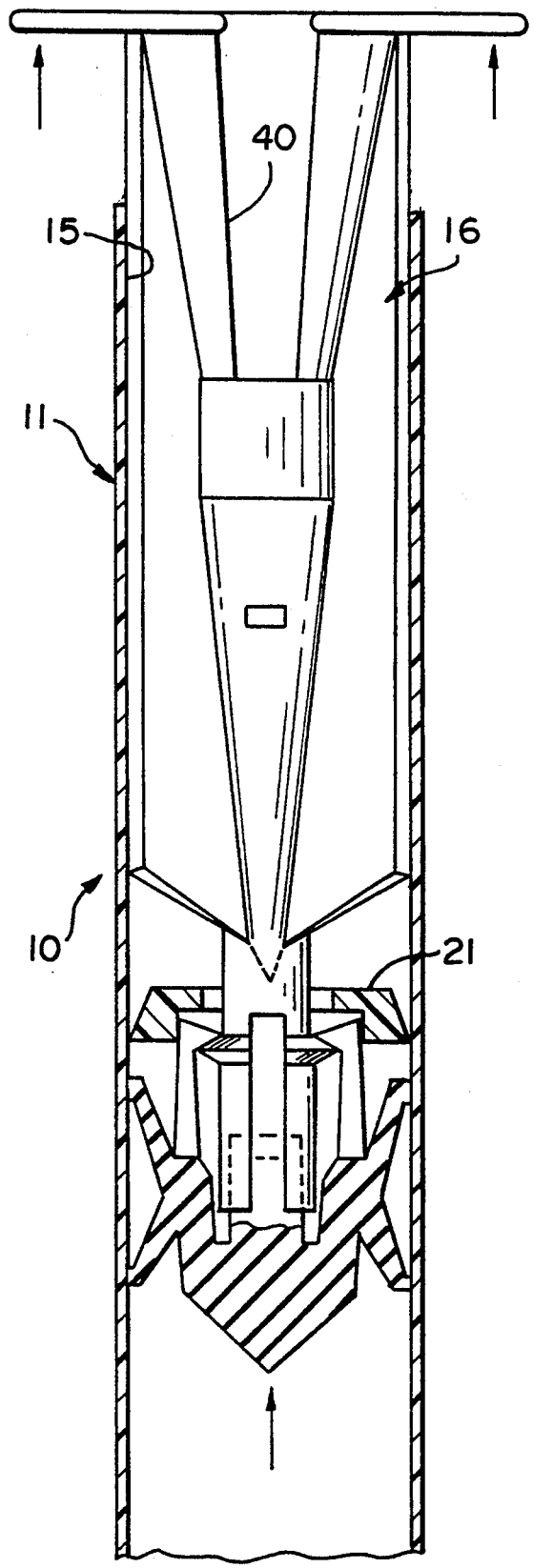

NON-REUSABLE SYRINGE WITH REMOVABLE PLUNGER USABLE AS A NEEDLE GUARD

This application is a continuation-in-part of copending application Ser. No. 07/985,301, filed Dec. 4, 1992, entitled Non-Reusable Syringe With Needle Guard, now abandoned which is, in turn, a continuation-in-part of application Ser. No. 07/802,628, filed Dec. 5, 1991, now U.S. Pat. No. 5,181,912, issued Jan. 26, 1993, and entitled Non-Reusable Syringe.

BACKGROUND OF THE INVENTION

Field of the Invention

This invention relates generally to hypodermic syringes, and more particularly, to a hypodermic syringe that is capable of use only once, and which has a part that is removable after use to serve as a needle guard.

It is frequently necessary to use hypodermic syringes for intravenous administration of fluids, or to withdraw fluids from the veins of a person during the course of treatment of an illness, or in routine diagnostic examinations. Hypodermic syringes used for this purpose are generally disposable, and are intended to be discarded after a single use by trained medical personnel.

Unless they are properly disposed of, these used syringes present a health hazard. One of the more serious concerns of health care workers is the danger of becoming accidentally infected with HIV-infected blood or other materials. Acquired Immune Deficiency Syndrome (AIDS) is now recognized as an epidemic of global proportion. In addition, there is an increasing recognition of a broad spectrum of severe HIV-associated diseases, including pneumonia, endocarditis, and pulmonary tuberculosis. Medical and rescue personnel are aware of these risks, and when possible, take precautions to avoid unnecessary exposure or contact with infectious materials.

However, if a used syringe has been left intact and not properly disposed of, medical and rescue personnel, custodial workers, and others, are exposed to the danger of being accidentally pricked with the contaminated needle in spite of the precautions that they might normally take. Such a needle could be mingled with soiled linens, bandages or other materials, and when these materials are gathered for disposal, the needle has the distinct potential of penetrating the skin of anyone handling the materials.

The used syringe could also fall into the hands of a drug addict or other person who may be inclined to reuse the syringe. Such persons typically reuse a syringe many times and share it with other addicts. If the syringe has been used to make an injection or to withdraw body fluid from a person having an infectious disease, all of those persons subsequently using the contaminated needle are at risk of acquiring the infectious disease.

Intravenous drug use is believed to account for most AIDS-related diseases in heterosexual men and women. This disease may also be transmitted to the children of infected adults, and to the sex partners of the infected persons, or to others, such as medical workers and rescue personnel, who may be inadvertently exposed to the blood of the infected person.

As AIDS-related diseases continue to grow, it is becoming increasingly more important to control the means by which these diseases are transmitted. Medical personnel should have reasonable assurance that they can perform their procedures without unnecessary risk of exposure to such infectious diseases, and without requiring time-consuming steps to render used syringes safe for subsequent handling.

To prevent such accidents from occurring, the needles should be broken from the used syringes, and/or encased in a protective sheath, and devices have been provided in the prior art for accomplishing this. For instance, needles have been joined to the syringe body through frangible connections so that the doctor, nurse or other medical personnel can easily break the needle from the syringe after it is used. Unfortunately, this is not always done during the urgency of medical treatment, or if it is, there still remains an exposed needle body.

Similar shortcomings exist with respect to guards or sheaths that have been provided to encase the used needle. Such guards generally comprise separate sleeves or cap members that enclose the needle before it is used and which must be removed and set aside during use of the syringe. It is intended that after use of the needle, the guard will again be placed over the needle. However, the guard may become misplaced during the medical procedure being performed and therefore not available for reuse. Even if it is not misplaced, the person responsible for safe handling of the syringe may not have the time, or take the time, to retrieve the guard and place it over the needle. Further, even if such a conventional guard is placed on the needle, it is capable of being removed, whereby the syringe could again be rendered capable of use.

In addition to an effective needle guard for used syringes, a means is needed to prevent sharing and reuse of syringes by intravenous drug abusers, and thereby to prevent the spread of infectious diseases caused by use of contaminated syringes. Since the major cause of spread of HIV, Hepatitis and similar diseases is through the repeated and/or shared use of contaminated hypodermic syringes and needles, a significant preventive measure would be the elimination of the ability of intravenous drug abusers to acquire syringes that could be used more than one time.

Accordingly, it would be desirable to have a disposable hypodermic syringe that is reliable in operation, simple and economical in construction, and in which a part of the syringe assembly itself is adapted as a needle guard after the syringe has been used for its intended purpose. It would further be desirable to provide a disposable syringe that is not capable of being reused after a single use.

SUMMARY OF THE INVENTION

The disposable syringe of the invention comprises a cylindrical syringe barrel of substantially conventional construction, having an open end and a suitable conventional fitting on the other end, such as a Luer lock adapter, or other means, for attaching a needle. A plunger or stem is reciprocable in the barrel and carries a piston on its inner end for developing vacuum or pressure, depending upon the direction of reciprocation of the piston and plunger in the barrel.

An essential feature of the present invention is the use of the plunger, itself, as a guard for the needle after the syringe has been used. To this end, the plunger has a cavity formed in it, shaped to receive the needle and to remain securely attached to the syringe after it has been placed over the needle. In use, the plunger is simply removed from the barrel after the syringe has been used, and placed over the needle. There is no separate member which must be retrieved and used for this purpose.

Moreover, in a preferred embodiment, an entry slot is formed through the side of the plunger at the open end, through which the needle may be initially laterally placed prior to being axially fully inserted into the plunger, to thereby minimize the risk of pricking the finger of the person placing the guard over the needle.

Additionally, a small quantity of glue is positioned in the plunger/guard to permanently adhesively secure the plunger/guard to the needle after it is placed in operative position on the needle, thereby rendering the needle incapable of reuse.

Further in accordance with the invention, the syringe is automatically rendered inoperable after a single use, so that it cannot be used again. In a conventional syringe, the piston is attached to the end of the plunger so that it will not become displaced from the plunger during use, even though the plunger and piston may be reciprocated many times in the barrel of the syringe. However, in the present invention, the piston is releasably attached to the end of the plunger by movable latch arms and a collar. The collar moves into a position to release the latch arms when the plunger and piston are reciprocated through one cycle rearwardly and then forwardly in the barrel. A subsequent reciprocal movement of the plunger rearwardly in the barrel results in the piston becoming separated from the plunger so that it cannot be reattached to the plunger without the use of a special tool used during its manufacture, thus rendering the syringe incapable of further use.

In the present invention the piston is preferably made of a synthetic plastic material, whereas in conventional syringe constructions the piston is normally made of a rubber material. To prevent set or "cold creep" of the seals of the plastic piston, a relief area is formed in the inner surface of the syringe barrel in the position occupied by the piston when it is in its at-rest, stored position fully inserted into the syringe barrel.

In an alternate construction, however, the piston used in the system of the invention may be made of rubber and still incorporate the novel features of the invention.

BRIEF DESCRIPTION OF THE DRAWINGS

The foregoing and other objects and advantages of the invention will become apparent from the following detailed description when considered in conjunction with the accompanying drawings, wherein like reference characters refer to like parts throughout the several views, and wherein:

FIG. 4 is an enlarged longitudinal sectional view of a syringe incorporating the plunger and piston assembly of FIG. 1, showing the components in their normal, at-rest condition at the bottom of the barrel;

FIG. 5 is a view similar to FIG. 4, showing the plunger and piston being withdrawn or moved rearwardly in the barrel;

BEST MODE FOR CARRYING OUT THE INVENTION

Figure 1:
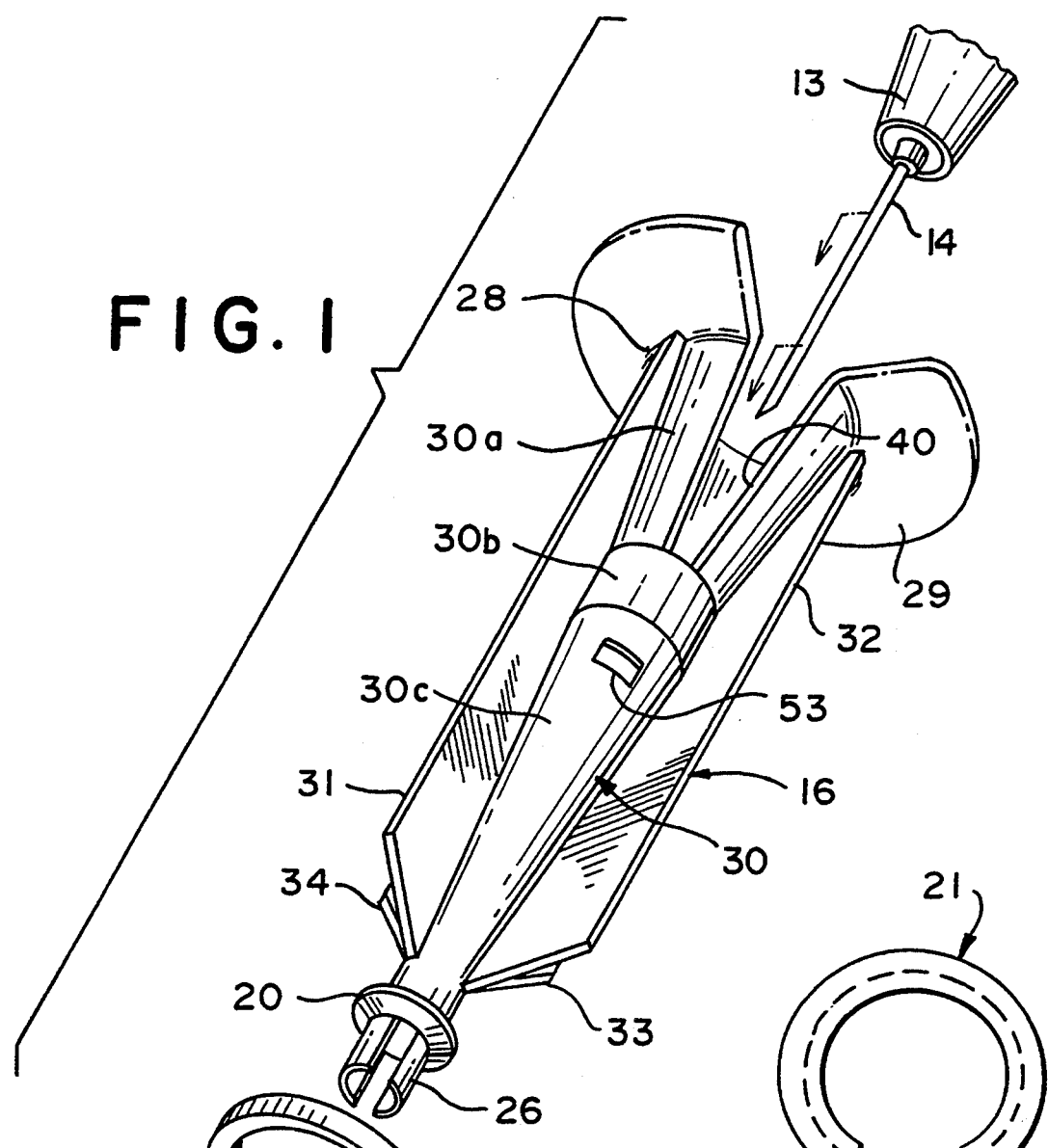
FIG. 1 is an exploded perspective view of a first form of plunger and piston assembly incorporating the features of the invention.

Referring more specifically to the drawings, a syringe in accordance with the invention is indicated generally at 10 in FIGS. 1–7. In this form of the invention, a cylindrical syringe barrel 11 has a forward end 12 with a suitable means, such as a Luer lock adapter 13, for attachment of a needle 14, and an open rearward end 15. A plunger 16 is reciprocable in the barrel, and carries a piston 17 at its forward end for drawing material into the plunger and discharging it through the needle.

The piston 17 is releasably connected to the plunger so that it is rendered inoperable after a single use. To this end, the piston has a plurality of rearwardly projecting latch arms 18 that are molded with a radially outwardly oriented bias, so that they assume the position shown in FIGS. 6 and 7 when they are unrestrained.

The free end of each latch arm has a radially inwardly directed detent 19 that is adapted to engage behind a retaining ring 20 on the forward end of the plunger to hold the piston to the plunger when the latch arms are urged inwardly to the position shown in FIGS. 4 and 5. The latch arms are held in this position by a retaining collar 21 engaged in encircling relationship over the free outer ends of the latch arms.

Figure 2:
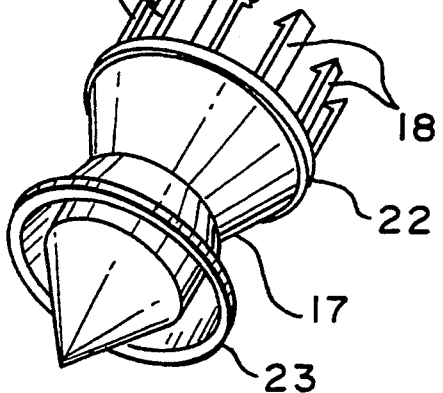
FIG. 2 is a top plan view of the collar used to hold the latch arms engaged with the plunger, showing the collar in its "as molded" condition.
Figure 3:
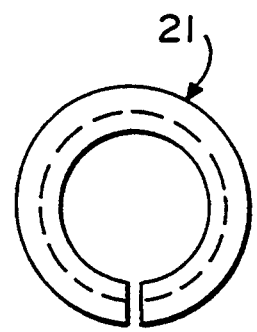
FIG. 3 is a top plan view similar to FIG. 2, showing the collar in its compressed condition after assembly in the barrel to hold the latch arms engaged with the plunger.
Figure 6:
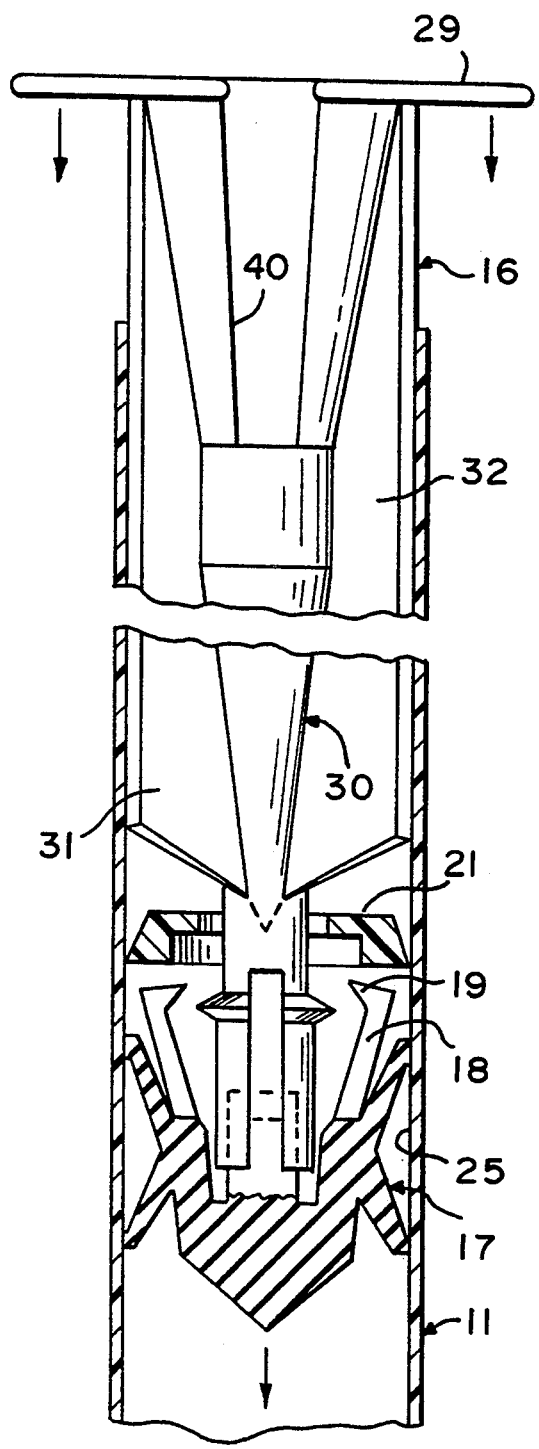
FIG. 6 is a view similar to FIG. 5, showing the plunger and piston being moved forwardly in the barrel.
Figure 7:
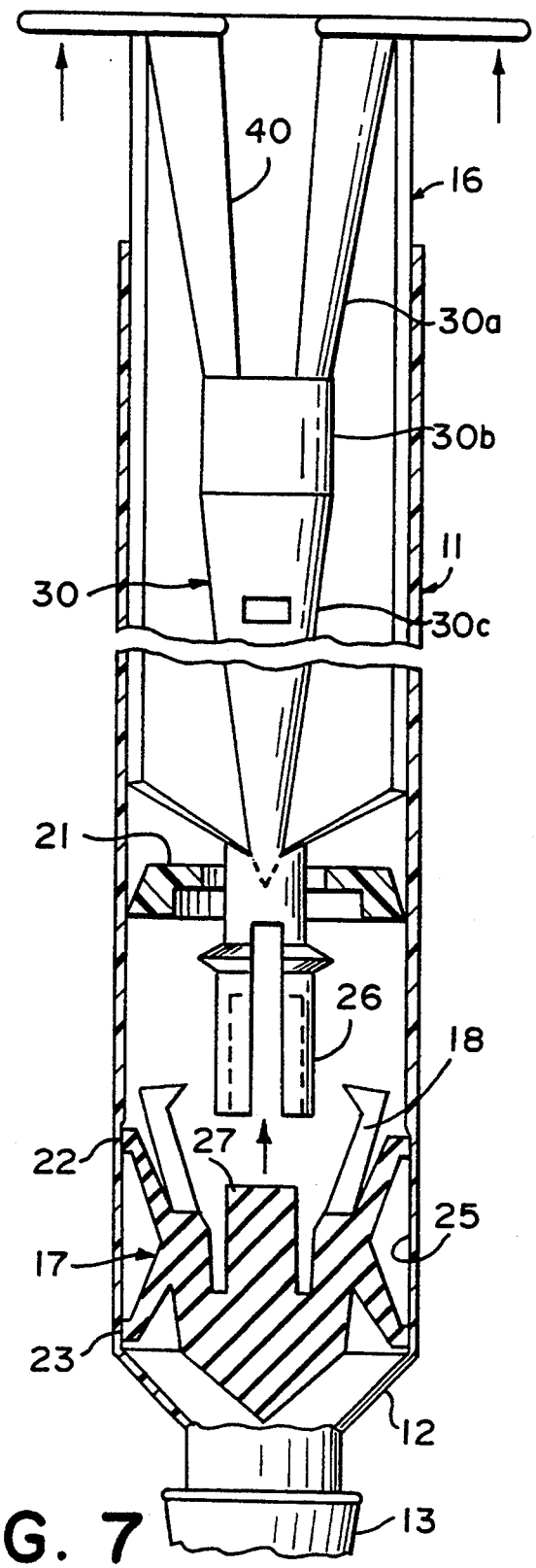
FIG. 7 is a view similar to FIG. 6, showing the plunger again being moved rearwardly in the barrel, and depicting how the collar and latch arms have become disengaged to release the piston from the plunger.

As seen best in FIGS. 2 and 3, the collar 21 comprises a split ring, and, as shown in FIG. 2, is molded with an outwardly biased configuration. When compressed and inserted into the syringe barrel, however, the collar assumes the position shown in FIG. 3.

The piston 17 may be made of any suitable material, but in the form shown is made of plastic, and has two oppositely oriented, outwardly flared sealing rings 22 and 23 for sliding engagement against the inner surface of the syringe barrel.

The inner surface of the barrel adjacent the end 12 is slightly diametrically enlarged at 25 to provide a relief area for the piston 17 when it is inserted fully into the barrel. This relief area prevents set of the piston seals 22 and 23 which might otherwise occur when the piston is made of plastic material and is stored in this position.

The plunger 16 is reciprocable in the barrel between a forward position inserted fully into the barrel, and a rearward position retracted or withdrawn in the barrel, and has a forward end 26 that telescopically engages with a central post 27 on the rearward side of the piston 17.

The rearward end 28 of the plunger has a radially enlarged operating flange 29 which may be gripped with the fingers and used to reciprocate the plunger in the barrel.

In this form of the invention, the plunger may have a generally X-shaped transverse cross-section, with a central body 30 and oppositely extending flanges 31, 32, 33 and 34 along diametrically opposite sides of the body to slidably support the plunger in the barrel.

An essential feature of the present invention is the construction of the plunger body 30 so that it is hollow and has a stepped configuration, including a larger tapered entry portion 30a adapted to receive the tapered portion 13 of the Luer adapter on the syringe barrel, an intermediate cylindrical portion 30b adapted to lock onto the cylindrical portion of the Luer Lock fitting of the syringe barrel, and a reduced diameter tapered portion 30c adapted to closely receive the needle 14.

Figure 13:
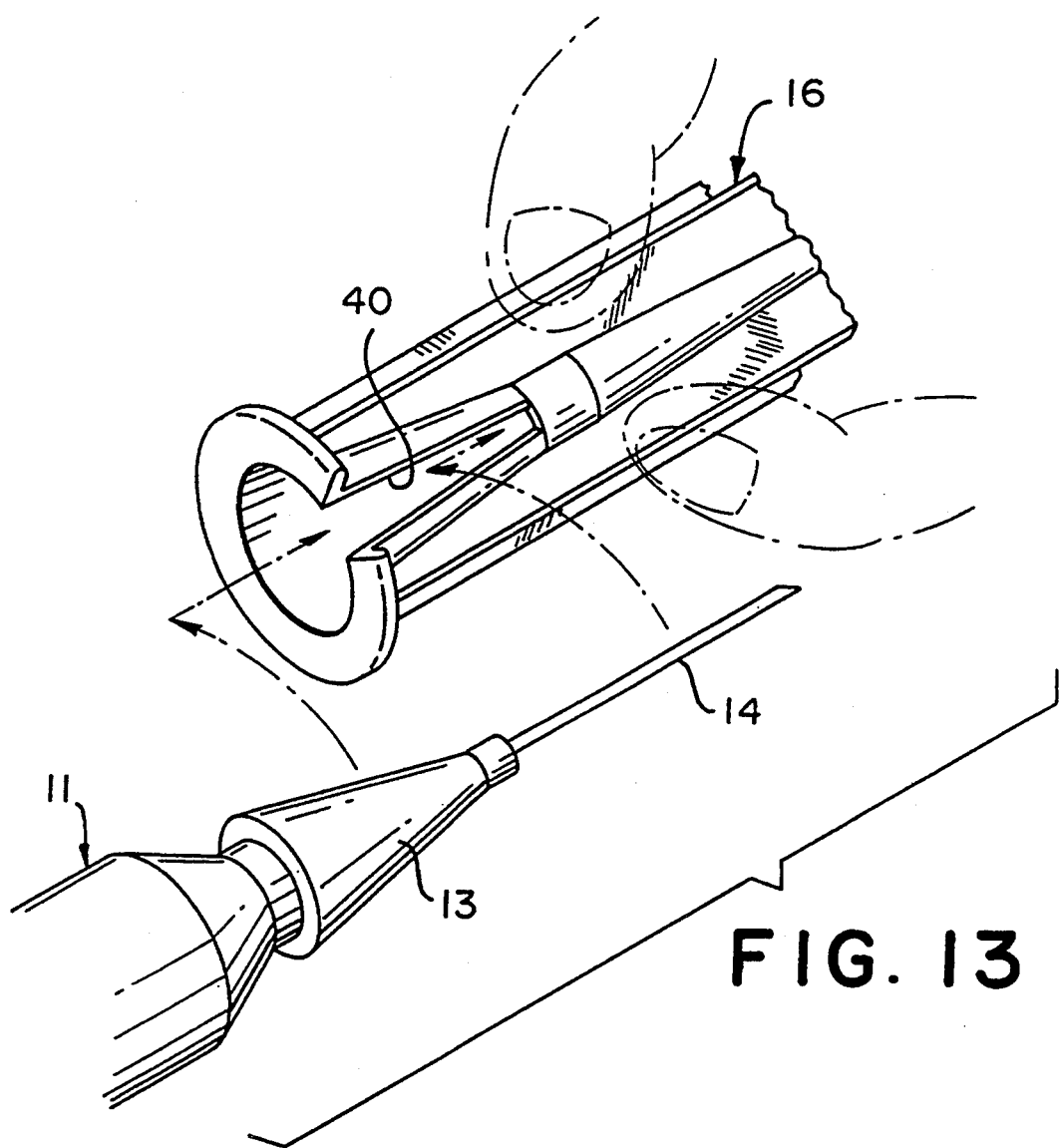
FIG. 13 is a somewhat schematic, fragmentary, exploded perspective view of the syringe of the invention, showing how the needle is initially laterally positioned in the slot in the plunger so that the point of the needle is shielded before it is moved axially into a fully seated position in the plunger.
Figure 14:
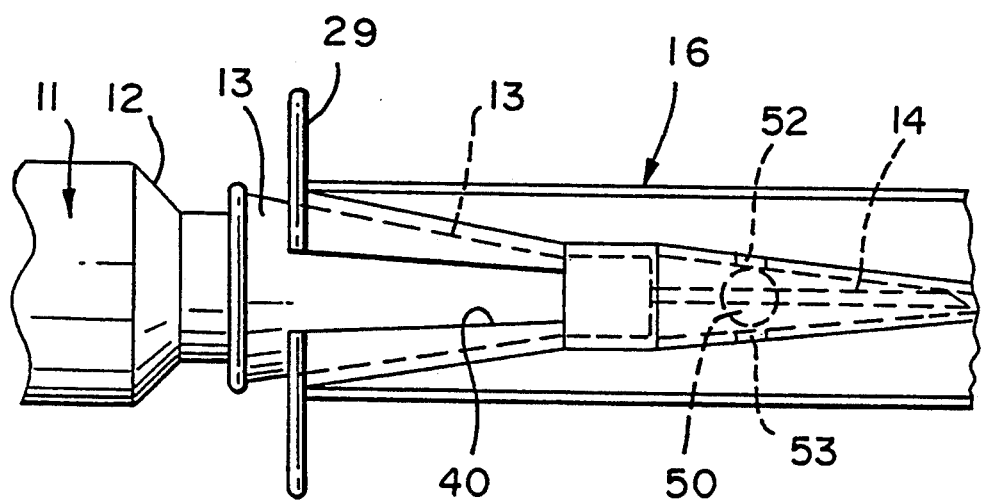
FIG. 14 is a fragmentary view, with portions broken away, depicting the relationship of the plunger and needle when the needle fully is seated in the plunger/guard.

After the syringe 10 has been used, it is a simple matter for the doctor, nurse or other medical personnel to simply withdraw the plunger 16 from the barrel 11 and place the plunger over the needle, with the portions 30a and 30b locking onto the Luer Lock adapter 13 of the syringe barrel, as shown in FIGS. 13 and 14. There is no need for the doctor, nurse or other person using the syringe to search for and retrieve a separate needle guard, as is presently necessary in the prior art.

To facilitate placement of the plunger over the needle and to reduce the danger of accidentally pricking oneself with the needle while accomplishing this, an elongate slot 40 is formed through the side of the plunger body, leading from the end 28 and terminating at the end of the tapered portion 30a. Thus, the needle may be laid sideways into the slot and then slid lengthwise to fully seat the needle in the plunger/guard. This eliminates the danger of missing the relatively small opening in the end of the plunger when attempting to insert the needle lengthwise into the guard.

A small envelope 50 containing an adhesive 51 is located in the hollow bore portion 30c of the plunger in a position to be pierced by the needle 14 as the plunger is placed over the needle. The envelope 50 is roughly the size of a BB and is located at a point in the bore where small openings 52 and 53 are formed during the molding process. When the needle pierces the envelope, the adhesive 51 escapes and flows into the space surrounding the needle and into the two small openings 52 and 53, thereby forming a mechanical lock between the needle and the plunger and preventing removal of the plunger after the adhesive has cured. It should also be noted that it is anticipated that a small quantity of the adhesive will enter the end of the needle as it passes through the envelope of adhesive, plugging the needle and preventing its use even if access to it should be gained.

Figure 8:
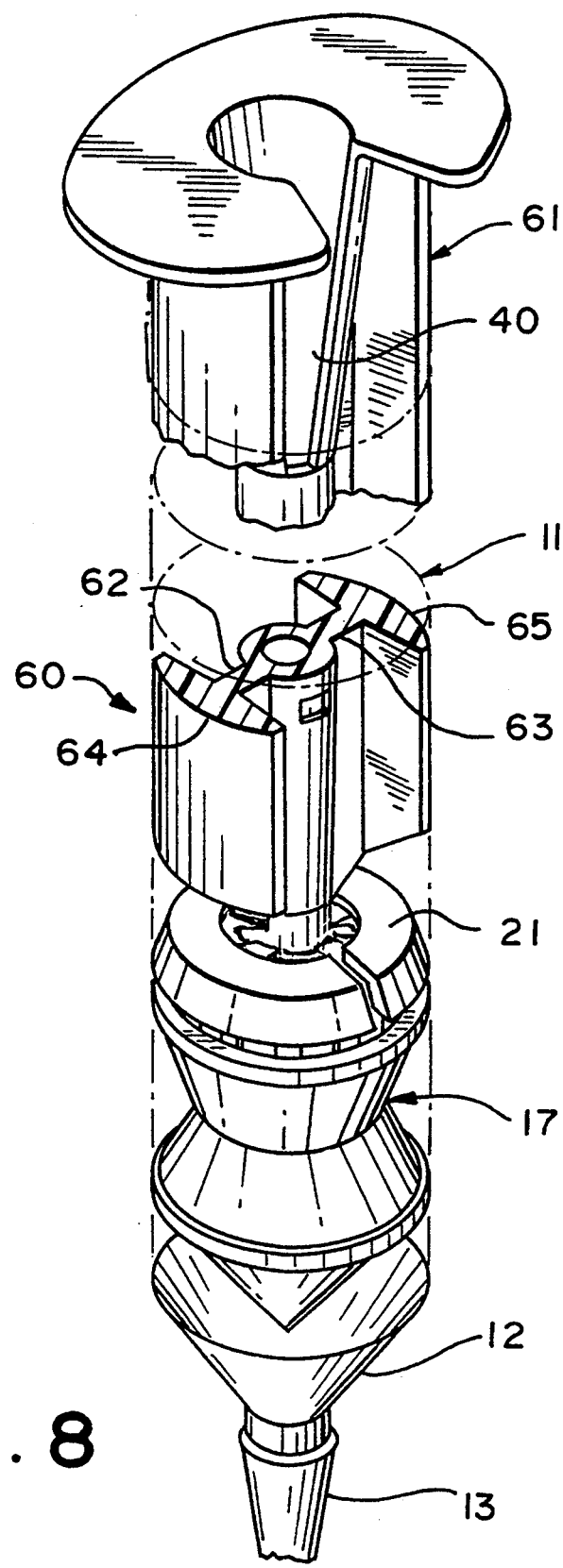
FIG. 8 is an enlarged perspective view of a modified syringe incorporating the features of the invention, with parts broken away and parts shown in section.
Figure 10:
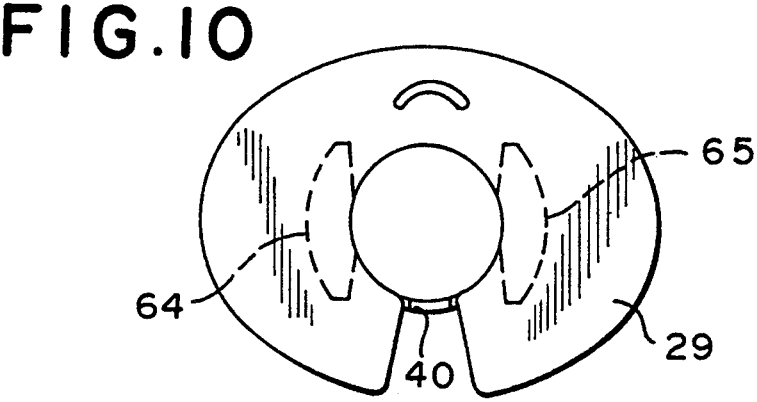
FIG. 10 is an end view of the syringe of FIG. 9.
Figure 9:
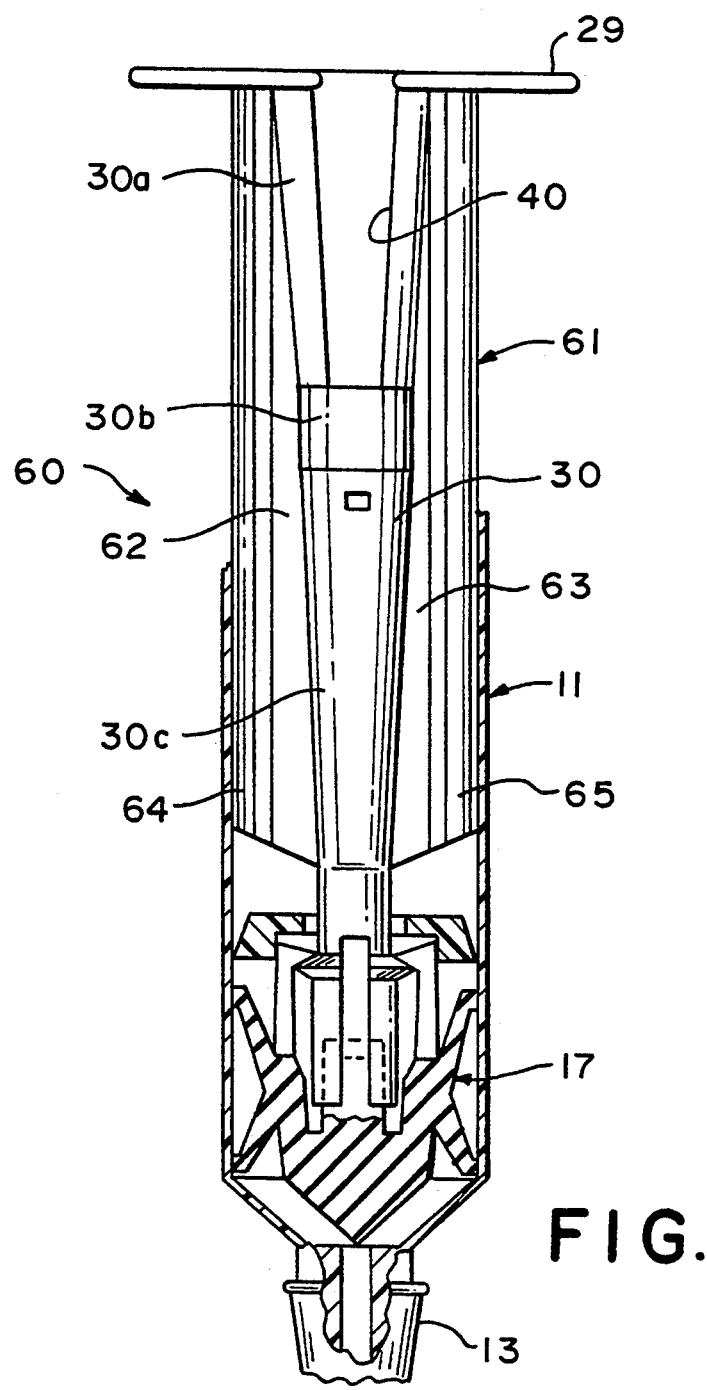
FIG. 9 is a longitudinal sectional view on a reduced scale, with portions broken away and portions shown in section, of the syringe assembly of FIG. 8.

A second form of the invention is indicated generally at 60 in FIGS. 8-10. The plunger 61 in this form of the invention also has a hollow central body 30, as in the previous form of the invention, with stepped diameter portions 30a, 30b and 30c for the same purposes as described in connection with the previous embodiment. However, rather than the X-shaped cross-section as previously described, the plunger in this form of the invention has a pair of laterally projecting webs 62 and 63 with oppositely directed circumferentially extending flanges 64 and 65 on their outer edges. In all other respects, this form of the invention functions the same and has all the advantages of the previous form of the invention.

Figure 11:
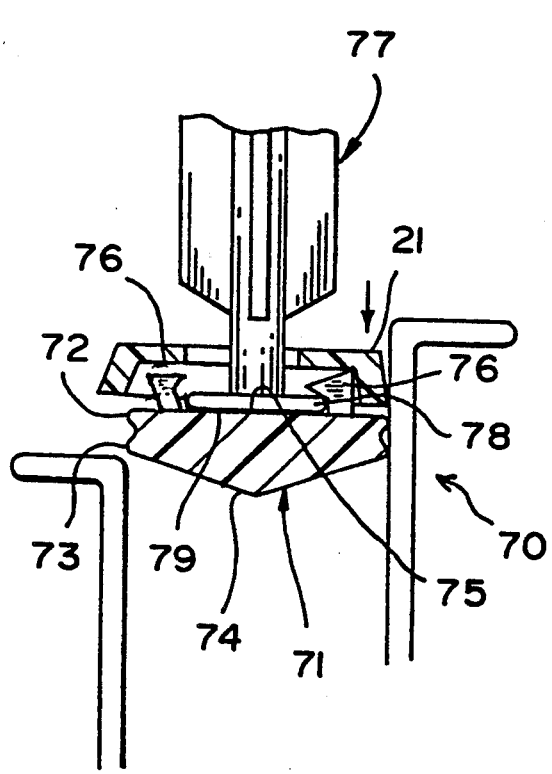
FIG. 11 is an enlarged, fragmentary sectional view of a further modified plunger and piston assembly, shown on the right hand side of the figure in operative, engaged position, and shown on the left hand side of the figure in disengaged, inoperative position.

A modified plunger and piston assembly is indicated generally at 70 in FIG. 11. In this form of the invention, the piston 71 is much shorter and disc-like than in FIG. 9, for example, and includes a pair of relatively closely axially spaced sealing beads or rings 72 and 73, a shallow, conically shaped nose portion 74, and a flat rear surface 75. A plurality of latch arms 76 on the rear surface of the piston are constructed and function the same as the latch arms described in connection with the first form of the invention.

The plunger 77, in turn, has an annular retaining flange 78 for cooperation with the latch arms, and a flat tip 79 on its forward end that engages the surface 75 on the piston.

A split retaining collar 21 identical to that previously described is adapted to normally encircle the free ends of the latching arms to retain them in engaged position behind the flange 78, as shown on the right hand side of FIG. 11, and is movable to an unlatched position, as shown on the left hand side of FIG. 11, when the plunger and piston are manipulated as described in connection with the previous form of the invention.

Figure 12:
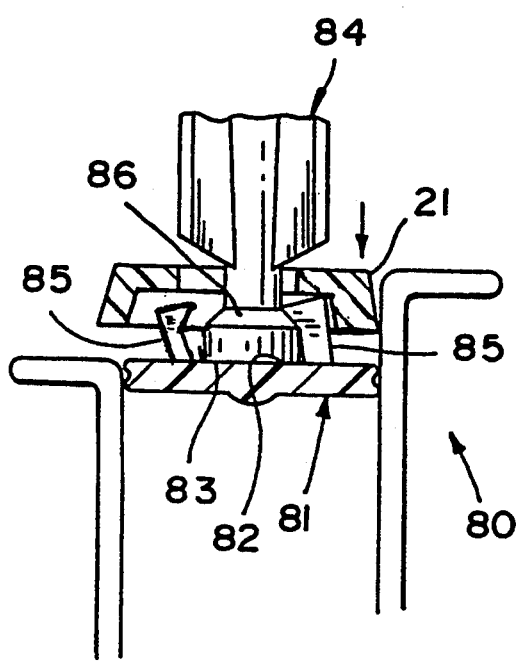
FIG. 12 is a view similar to FIG. 11 of another modified plunger and piston assembly.

A further modified plunger and piston assembly is indicated generally at 80 in FIG. 12. In this form of the invention, the piston 81 is essentially disc shaped, with a flat rear surface 82 for cooperation with the flat tip 83 of the plunger 84. A plurality of latching arms 85 are carried by the piston for cooperation with a retaining flange 86 on the forward end of the plunger to hold the piston assembled to the plunger when the split retaining collar 21 is in encircling relationship around the free ends of the latching arms. The collar and latch arms are releasable when the plunger and piston are manipulated as described previously.

During assembly of the syringe of the invention, the syringe barrel, plunger, piston and collar are positioned in relation to one another as shown in the left hand side of FIGS. 11 and 12, for example, the collar is compressed around the free ends of the latch arms, and the assembly is then inserted into the barrel through the open rearward end thereof.

While the piston has been described herein as made of plastic, it should be understood that it may equally as well be made of rubber, as described in copending application Ser. No. 07/802,628. In such event, the piston itself may be constructed differently in the area where it seals with the barrel, but the latching mechanism is substantially identical to that previously described, and the hollow body for encasing the needle is the same as before.

The syringe of the invention is simple and economical in construction, and yet it provides an entirely different structure and function as compared with a conventional syringe, i.e., the plunger doubles as a needle guard after the syringe has been used, and the piston is connected to the plunger through a latched construction that automatically disables the syringe after a single use.

While the invention has been illustrated and described in detail herein, it is to be understood that various modifications may be made therein without departing from the spirit and scope of the invention, as defined by the appended claims.

What is claimed is:

1. A non-reusable syringe having a built-in needle guard, comprising:
   an elongate cylindrical barrel having adapter means on one end for attachment of a needle, and an open other end;
   a needle secured to said adapter means on said one end of the barrel; an elongate plunger reciprocable in the barrel between a forward position in the barrel and a retracted position, said plunger having a forward end in the barrel and a rearward end accessible exteriorly of the barrel for operating the plunger;
   a piston carried on the forward end of the plunger for effecting a sliding seal with the barrel to draw material into the barrel and discharge it therefrom through said one end upon reciprocating motion of the plunger and piston in the barrel;
   said plunger having a hollow bore formed longitudinally through a central portion thereof, said bore including a first portion for cooperative locking engagement with the adapter means on the barrel and a second portion for receipt of the needle, whereby the plunger may be withdrawn from the barrel and placed in shielding relationship over the needle after the syringe has been used for its intended purpose;
   said plunger having an elongate slot formed in a side wall thereof, communicating with said bore and extending from said plunger open end toward the forward end, so that the plunger may be initially positioned laterally over said needle and then moved axially with respect thereto to fully seat the needle in the plunger; and
   a small ampoule containing a liquid adhesive that cures in the presence of oxygen located in the second portion of the hollow bore in position to be pierced by the needle when the plunger is removed from the barrel and placed over the needle, whereby the needle and plunger are adhesively secured together.

2. A syringe as claimed in claim 1, wherein:
   the bore is formed in the plunger from the rearward end thereof, and terminates in a distal, closed end of the second portion.

3. A syringe as claimed in claim 1, wherein:
   the piston is detachably connected to the plunger by releasable latch means that automatically disengages when the piston and plunger are reciprocated through one complete cycle of operation rearwardly and forwardly in the barrel.

4. A syringe as claimed in claim 3, wherein:
   the bore is formed in the plunger from the forward end thereof, and terminates in a distal, closed end of the second portion, and wherein detachment of said piston from said plunger exposes said bore so that the plunger may be used as a needle guard.

5. A syringe as claimed in claim 4, wherein:
   a quantity of adhesive is contained within the bore in a position to be pierced by the needle when the plunger is placed over the needle, said adhesive serving to fix said plunger on said barrel in shielding relationship to said needle.

6. A syringe as claimed in claim 3, wherein:
   the releasable latch means comprises a plurality of latching arms carried by the piston, said latching arms having free ends with detents thereon for engagement behind a retaining ring on the plunger to hold the piston to the plunger, said arms being molded with a normal, at-rest position spaced away from the retaining ring; and
   a split retaining collar normally engaged around the free ends of the latching arms, in encircling relationship thereto, to urge the latching arms inwardly toward the retaining ring on the plunger so that the detents on the latching arms normally engage behind the retaining ring on the plunger.

7. A syringe as claimed in claim 1, wherein:
   the piston is made of plastic and has outwardly biased yieldable seals thereon for sealing, sliding engagement with an inner surface of the syringe barrel; and
   the syringe barrel has an enlarged diameter inner surface portion at its forward end, defining a relief area for the piston when it is in a stored position to prevent set or creep of the seals, whereby an effective seal is maintained between the piston and barrel.

8. A non-reusable syringe, comprising:
   an elongate cylindrical barrel having adapter means on one end for attachment of a needle, and an open other end;
   an elongate plunger reciprocable in the barrel between a forward position in the barrel and a retracted position, said plunger having a forward end in the barrel and a rearward end accessible exteriorly of the barrel for operating the plunger;
   a piston carried on the forward end of the plunger for effecting a sliding seal with the barrel to draw material into the barrel and discharge it therefrom through said one end upon reciprocating motion of the plunger and piston in the barrel;
   said piston being releasably connected to the plunger by releasable latch means comprising a plurality of latching arms carried by the piston, said latching arms having free ends with detents thereon for engagement behind a retaining ring on the plunger to hold the piston to the plunger, said arms being molded with a normal, at-rest position spaced away from the retaining ring;
   a split retaining collar normally engaged around the free ends of the latching arms in encircling relationship thereto to urge the latching arms inwardly toward the retaining ring on the plunger so that the detents on the latching arms normally engage behind the retaining ring on the plunger to hold the piston to the plunger, but said collar becomes disengaged from the free ends of the latching arms upon forward motion of the plunger and piston in the barrel, whereby said latching arms move away from the retaining ring and the piston becomes disengaged from the plunger upon subsequent rearward movement of the plunger in the barrel; and
   a small ampoule containing a liquid adhesive that cures in the presence of oxygen located in the second portion of the hollow bore in position to be pierced by the needle when the plunger is removed from the barrel and placed over the needle, whereby the needle and plunger are adhesively secured together.

9. A syringe as claimed in claim 1, wherein:

the plunger has small openings in a sidewall thereof adjacent the location of the ampoule of adhesive, whereby when the ampoule is pierced the liquid adhesive will flow into the openings prior to curing and thereby form a mechanical lock between the adhesive, needle and plunger after the adhesive cures.

10. A syringe as claimed in claim 9, wherein:

said plunger has an elongate slot formed in a side wall thereof, communicating with said bore and extending from said plunger open end toward the forward end, so that the plunger may be initially positioned laterally over said needle and then moved axially with respect thereto to fully seat the needle in the plunger.

* * * * *